United States Patent [19]
Hirayama et al.

[11] Patent Number: 4,946,378
[45] Date of Patent: Aug. 7, 1990

[54] ARTIFICIAL INTERVERTEBRAL DISC

[75] Inventors: Yasuhiko Hirayama; Haruko Ikata; Satoshi Ojima; Hiromi Matsuzaki, all of Tokyo, Japan

[73] Assignee: Asahi Kogaku Kogyo K.K., Tokyo, Japan

[21] Appl. No.: 274,960

[22] Filed: Nov. 22, 1988

[30] Foreign Application Priority Data

Nov. 24, 1987 [JP] Japan .................. 62-295811

[51] Int. Cl.$^5$ .............................. A61F 2/44
[52] U.S. Cl. ....................... 623/17; 623/20; 128/69; 606/61
[58] Field of Search .............. 623/17, 20; 128/69, 128/92 YM

[56] References Cited

U.S. PATENT DOCUMENTS

| | | |
|---|---|---|
| 3,867,728 | 2/1975 | Stubstad et al. . |
| 3,875,595 | 4/1975 | Froning . |
| 4,044,170 | 8/1977 | Scharbach et al. . |
| 4,366,183 | 12/1982 | Ghommidh et al. ............ 623/16 |
| 4,553,273 | 11/1985 | Wu . |
| 4,759,766 | 7/1988 | Buettner-Janz et al. ............ 623/17 |

FOREIGN PATENT DOCUMENTS

| | | |
|---|---|---|
| 0176728 | 4/1986 | European Pat. Off. . |
| 0202908 | 11/1986 | European Pat. Off. . |
| 2263842 | 7/1974 | Fed. Rep. of Germany . |
| 0895433 | 1/1982 | U.S.S.R. ............... 623/17 |

OTHER PUBLICATIONS

Arch Jpn Chir 54(1), pp. 16-22, Jan. 1985.

Primary Examiner—Randall L. Green
Assistant Examiner—Stephanie L. Iantorno
Attorney, Agent, or Firm—Sandler, Greenblum & Bernstein

[57] ABSTRACT

An artificial intervertebral disc comprises a pair of end bodies which are provided, on their outer surfaces, with apatite layers. The disc includes a medical synthetic polymeric intermediate which is held between the end bodies through connecting members.

12 Claims, 2 Drawing Sheets

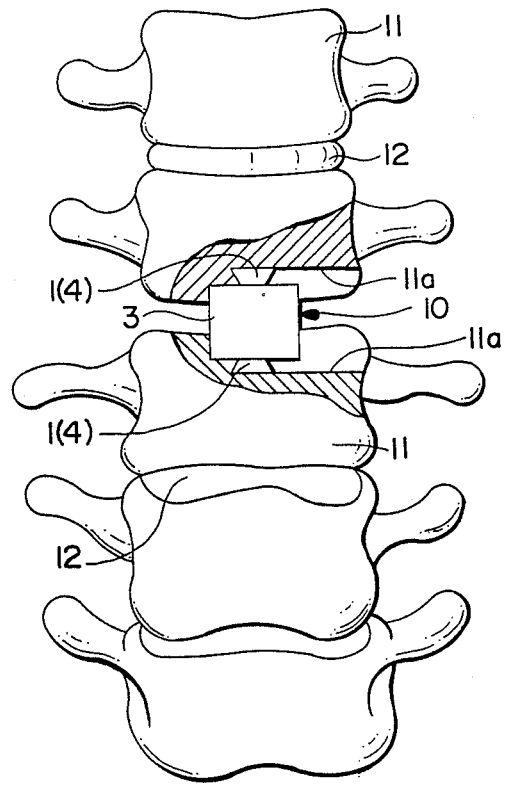
Fig_3

ARTIFICIAL INTERVERTEBRAL DISC

BACKGROUND OF THE INVENTION

1. Field of the Invention

The present invention relates to an artificial intervertebral disc (i.e., a movable vertebral body spacer) which can be implanted in a portion of a removed intervertebral disc to surgically treat a hernia of the intervertebral disc, or an injury of a cervical vertebra or the like.

2. Description of Related Art

A herniated intervertebral disc causes a patient to feel a severe pain due to the spinal nerves being pressed by a central nucleus pulposus, which is deviated by regressive change in the intervertebral disc. There are several kinds of hernias of intervertebral discs, most of which are those of the lumbar part. There is also a hernia of the intervertebral disc of the neck, which is caused by an external wound resulting from a fall, a traffic accident, or the like. It is also known that a hernia can be suddenly caused at night or at day time.

A hernia of an intervertebral disc, if relatively slight, can be treated by fixing the intervertebral disc, but if it is serious, a surgical operation is necessary. In conventional surgical treatments (i.e., operations), after the injured intervertebral disc is removed, a bone is implanted between upper and lower vertebral bodies. In the bone implantation, either a part of the iliac bone of the patient, or an artificial bone made of alumina or apatite, is used. In these methods, however, the vertebral bodies which are naturally movable per se are immovably fixed and, accordingly, the vertebral bodies can not move relative to each other.

There has been a long need for the development of a movable biomaterial which is implanted between vertebral bodies.

SUMMARY OF THE INVENTION

The primary object of the present invention is to eliminate drawbacks of the prior art mentioned above by providing an artificial intervertebral disc exhibiting biocompatibility, which disc can be easily implanted between vertebral bodies, which enables the vertebral bodies to move after implanting, and which does not cause discomfort to the patient due to the presence of the artificial intervertebral disc.

To achieve the objects mentioned above, an artificial intervertebral disc according to the present invention has a pair of end bodies having apatite layers on their outer surfaces, and a medical synthetic polymeric intermediate material having an elasticity; the intermediate material is held between the end bodies through connecting members.

Preferably, the end bodies of the artificial intervertebral disc, according to one embodiment of the present invention, are made of metal to increase the strength of the intervertebral disc. The end bodies are provided, on their outer surfaces, with apatite layers or coatings so as to exhibit biocompatibility. The apatite layers can be formed, for example, by spraying. Preferably, the coefficients of thermal expansion of the apatite of the apatite layers and the metal of the end bodies are identical to each other. Titanium can be used as the metal from which the end bodies are made.

The spraying can be performed, for example, by plasma spraying of apatite powders.

The apatite layers are preferebly made of hydroxyapatite. It may be, however, not necessarily pure, and may contain apatites in which the hydroxy ions are substituted by fluorine or chlorine atoms and/or in which the calcium atoms are substituted by the other metal atoms.

Preferably, the thickness of the apatite layers is usually 0.1 mm~0.5 mm.

Preferably, the end bodies have projections which can be properly fitted into the vertebral bodies so as not to come out of the associated vertebral bodies.

In the present invention, the elastic medical synthetic polymeric intermediate can be made of any rubber having biocompatibility, such as silicone rubber, polyvinyl alcohol, polyurethyane resin, or the like. The medical synthetic polymer referred to herein has properties of chemical inactivity; no degeneration by tissue-liquid, such as blood or humor; no vital reaction such as circumferential inflammation; no reaction to foreign matter (i.e., implants), non-carcinogenic; non-allergic reaction; no decrease in tensile strength and in elasticity even after being implanted in the vital body for a long period of time; no degeneration due to disinfection, such as boiling, chemicals or gas sterilization; and, simple and inexpensive machining and molding, etc.

The connecting members for connecting the end bodies and the synthetic polymeric intermediate can be made of a material having proper strength, such as titanium, stainless steel, or the like.

BRIEF DESCRIPTION OF DRAWINGS

The invention will be described below in detail with reference to the accompanying drawings, in which:

FIG. 3 is a schematic view of an artificial intervertebral disc which is inserted between vertebral bodies.

DETAILED DESCRIPTION OF EMBODIMENTS

Figure 1:
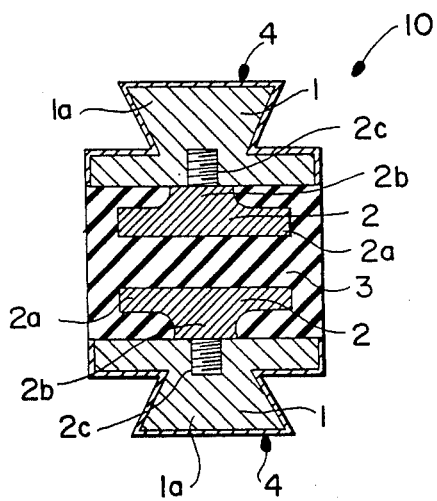
FIG. 1 is a sectional view taken along the line I—I in FIG. 2, showing an artificial intervertebral disc according to one embodiment of the present invention.
Figure 2:
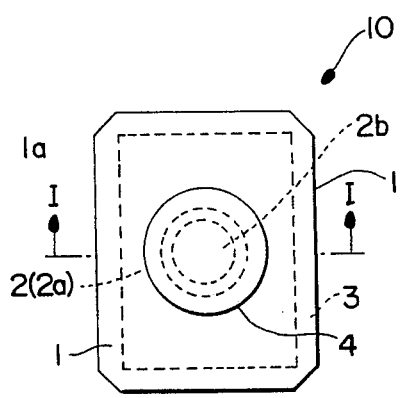
FIG. 2 is a plan view of an artificial intervertebral disc according to one embodiment of the present invention.

An artifical intervertebral disc 10 according to the present invention has a pair of end bodies 1 and a medical synthetic polymeric intermediate (member) 3 which is held between the end bodies 1 through connecting members 2. The medical synthetic polymeric intermediate 3 has a desired elasticity. The end bodies 1 are provided, on their outer surfaces, with apatite layers 4.

The end bodies 1 which are made of titanium are in the form of a rectangular parallelepiped and have outwardly extending center projections 1a in the form of an inverted frustrated cone. The projections 1a can be embedded in openings which will be formed in the vertebral bodies to oppose the adjacent vertebral bodies by a surgical operation. The projections 1a effectively prevent the end bodies 1 from coming out of the associated vertebral bodies.

The connecting members 2, which are made of titanium or stainless steel, have embedded portions 2a which are in the form of a rectangular parallelepiped and which are slightly smaller than the end bodies 1, cylindrical projections 2b which are provided on the center portions of the embedded portions 2a to come into abutment with the associated end bodies 1, and screws (threaded portions) 2c which are provided on the projections 2b and which are adapted to be screwed in the associated end bodies 1.

The outer apatite layers 4 on the end bodies 1 can be formed, for example by plasma spraying, which is per se known.

The thickness of the apatite layers 4 is preferably 0.1~0.5 mm.

A pair of end bodies 1 which are connected to the connecting members 2 by respective screws (threaded portions) 2c are spaced from and opposed to one another at a proper distance in a mold (not shown). After that, a synthetic rubber latex is fed in between the end bodies 1 and is then cured to form a medical synthetic polymeric intermediate 3 in which the connecting members 2 are embedded. In the artificial intervertebral disc 10 thus obtained, the medical synthetic polymeric intermediate 3 also occupies the spaces between the embedded portions 2a of the connecting members 2 and the associated end bodies 1. Since the embedded portions 2a are substantially analogous to and slightly smaller than the end bodies 1, the end bodies 1 are connected by the synthetic polymeric intermediate 3. Namely, there is no possibility of separation of the end bodies 1 from the associated connecting members 2 even after the artificial intervertebral disc 10 is embedded between the vertebral bodies.

The artificial intervertebral disc (spacer) 10 of the present invention is movable due to the flexibility of the medical synthetic polymeric intermediate 3. Accordingly, the medical synthetic polymeric intermediate 3 has a sufficient thickness to exhibit flexibility. The thickness of the medical synthetic polymeric intermediate 3, which depends on the total size of the spacer 10 and the size of the connecting members 2 etc. is usually 5~35 mm and preferably 10~30 mm.

FIG. 3 schematically shows an artificial intervertebral disc 10 which is inserted between adjacent vertebral bodies 11 of the lumbar part of the neck. The adjacent vertebral bodies 11 have openings 11a formed therein in which the associated projections 1a of the end bodies 1 of the artificial intervertebral disc 10 are embedded. Numeral 12 designates sound intervertebral discs.

Since the medical synthetic polymeric intermediate having flexibility is held between the end bodies 1, the artificial intervertebral disc according to the present invention can be elastically deformed in accordance with movement of the vertebral bodies 11. As a result, the spinal cord portion in which the artificial intervertebral disc 10 of the present invention is implanted, is movable, and accordingly, does not have an adverse influence on the sound vertebral bodies. In particular, the artificial intervertebral disc 10 of the present invention can be advantageously implanted in the neck, so that the patient can move the neck without feeling discomfort. Furthermore, since the artificial intervertebral disc of the present invention has apatite layers 4 provided on the outer surfaces of the end bodies 1 so as to provide a biocompatibility, and since the medical synthetic polymeric intermediate 3 is formed by a molded rubber, no adverse influence is imparted to the vital tissues and functions.

It should be noted that the shapes of the end bodies 1 and the connecting members 2 are not limited to those illustrated in the drawings, and can be modified without deviating from the scope of protection of the invention.

We claim:

1. An artificial intervertebral disc comprising a pair of end bodies, and a medical synthetic polymeric intermediate which is held between the end bodies via connecting members, said connecting members including projections for abutting associated end bodies, and embedded portions which are embedded in said medical synthetic polymeric intermediate, the transverse dimension of each said embedded portion being larger than the transverse dimension of each said projection, whereby said connecting members are connected to said medical synthetic polymeric intermediate so that resistance and elasticity occur through said connecting members when both compression and tensile forces are applied.

2. An artificial intervertebral disc according to claim 1, wherein said end bodies are made of titanium.

3. An artificial intervertebral disc according to claim 1, wherein said end bodies are made of stainless steel.

4. An artificial intervertebral disc according to claim 1, wherein said connecting members are made of stainless steel.

5. An artificial intervertebral disc according to claim 1, wherein said connecting members are made of titanium.

6. An artificial intervertebral disc according to claim 1, wherein said connecting members have screws for connecting said members to associated end bodies.

7. An artificial intervertebral disc to be implanted between vertebral bodies, according to claim 1, wherein said end bodies have projections which are adapted to be engaged in associated vertebral bodies.

8. An artificial intervertebral disc according to claim 1, wherein said medical synthetic polymeric intermediate is elastic.

9. An artificial intervertebral disc according to claim 8, wherein said medical synthetic polymeric intermediate is made of a material selected from silicone rubber, polyvinyl alcohol, and polyurethane.

10. An artificial intervertebral disc according to claim 1, where said end bodies include outer surfaces and said outer surfaces include apatite layers.

11. An artificial intervertebral disc according to claim 10, wherein said apatite layers and said end bodies are made of materials having coefficients of thermal expansion substantially identical to each other.

12. An artificial intervertebral disc according to claim 1, wherein each end body is substantially in the shape of an inverted frustrum cone.

* * * * *